United States Patent [19]

Jarvis, Jr. et al.

[11] Patent Number: 4,614,651

[45] Date of Patent: Sep. 30, 1986

[54] INTERFERON EPSILON

[75] Inventors: Allan P. Jarvis, Jr., Newburyport; David I. Kosowsky, Newton, both of Mass.

[73] Assignee: Damon Biotech, Inc., Needham Heights, Mass.

[21] Appl. No.: 628,327

[22] Filed: Jul. 6, 1984

Related U.S. Application Data

[63] Continuation-in-part of Ser. No. 397,610, Jul. 12, 1981, abandoned.

[51] Int. Cl.$^4$ .................... A61K 45/02; C12P 21/00
[52] U.S. Cl. .................................. 424/85; 435/68; 435/804; 530/351
[58] Field of Search ............... 435/68, 172.3; 424/85; 260/112 R; 530/351

[56] References Cited

U.S. PATENT DOCUMENTS

| | | | |
|---|---|---|---|
| 3,256,152 | 6/1966 | Lampson | 424/85 |
| 3,560,611 | 2/1971 | Chany et al. | 424/85 |
| 3,660,564 | 5/1972 | Yoneda et al. | 424/85 |
| 3,699,222 | 10/1972 | Isaacs et al. | 424/85 |
| 4,016,036 | 4/1977 | Green | 435/240 |

FOREIGN PATENT DOCUMENTS 02674 10/1981 PCT Int'l Appl. .

OTHER PUBLICATIONS

Chemical Abstracts, vol. 94, p. 441, Abst. No. 206918e, 1981.
Ferreira, P., et al., Interferon; Properties and Clinical Uses, pp. 121–126, 1979.
Fournier, F., et al., J. Immunology, vol. 99, pp. 1036–1040, 1967.
Jameson, et al., Archives of Virology, vol. 62, pp. 209–219, 1979.
Eihorn et al., J. Gen. Virol, vol. 35, pp. 573–577, 1977.
Goeddel et al., Nature, vol. 287, pp. 411–416, 1980.
The Interferon System, W. E. Stewart, II, 1981, Springer-Verlag/Wien.

*Primary Examiner*—Blondel Hazel
*Attorney, Agent, or Firm*—Lahive & Cockfield

[57] ABSTRACT

Disclosed is a new material having antiviral activity designated interferon epsilon. The material may be produced, for example, by exposing primary, diploid human epithelial cells to a virus and then incubating the cells under conditions in which the new interferon is produced and is secreted into the culture medium. The material is antigenically distinct from interferon alpha, interferon beta, and interferon gamma, and displays marked antiviral activity in human epithelial cells but no detectable activity in other cell types.

13 Claims, 1 Drawing Figure

INTERFERON EPSILON

REFERENCE TO RELATED APPLICATIONS

This application is a continuation-in-part of copending application Ser. No. 397,610, entitled Interferon-E filed July 12, 1981, now abandoned.

BACKGROUND OF THE INVENTION

This invention relates to a novel composition of matter (hereinafter called interferon epsilon or interferon E) useful, for example, in human epithelial cell cultures as an anti-viral agent, to processes for producing the material, and to processes for treating human epithelial cells so as to resist viral infection.

Interferons are materials which have antiviral properties. They are produced by certain types of cells which have been stimulated by exposure to a virus, certain nucleic acids, or antigen/mitogen complexes. Interferons are extremely potent drugs which show great promise as clinical antiviral and anti-tumor agents.

There are currently three known types of human interferon: interferon alpha, produced from human leukocytes or lymphoblastoid cells; interferon beta, produced from fibroblasts; and interferon gamma, produced from human T-lymphocytes. All three are secreted by the respective cells after the cells are stimulated by viruses or analogous challenges. Human interferons may be differentiated from each other by type-specific antibody reactions or protein sequencing.

In the past, the antiviral activity of each particular type of interferon has been measured by its ability to protect human fibroblast cells in culture. A conventional antiviral unit of interferon is that concentration which protects one-half the cells in a human fibroblast culture from challenge with Vesicular Stomatitis Virus at a standard concentration.

Antiviral activity has been detected in other cells of human and of animal origin. Interference in the multiplication of influenza virus was first detected by Issacs and Lindenmann (1957) in cultures of chicken chorioallantoic membrane. Another example is the Hela cell line which is a transformed cancer cell of epithelial (cervical) origin as reported by G. Gey et al. in Cancer Research, Vol. 12, pp. 264–265, 1952. Various transformed or neoplastic cell lines originally derived from human epithelial tissue can be stimulated to produce interferon. See "Production of Interferon by Human Tumor Cell Lines", Jameson et al, *Archives of Virology* 62, 209–219 (1979).

In U.S. patent application Ser. No. 397,610, now abandoned, the present applicants disclosed the existence of a new material, called interferon epsilon, and described a method of producing it. As described in that application, an epithelial cell culture of human epidermal origin (keratinocytes) was grown and challenged to produce interferon. The interferon was secreted by the cells into the culture medium and subsequently partially purified by affinity chromatography. The interferon thus purified was shown to demonstrate characteristics distinct from the known alpha, beta, and gamma interferons.

SUMMARY OF THE INVENTION

It has been discovered that a novel and unique antiviral material, interferon epsilon, is produced by human epithelial cells, especially keratinocytes, that the new material is antigenically distinct from interferon alpha, beta, and gamma, and that the new material has marked antiviral properties in human epithelial cells but no detectable activity on other types of human cells. The new material appears to have a molecular weight of about 20,000 daltons as determined by SDS polyacrylamide gel electrophoresis and appears to be species specific. Interferon epsilon has displayed no antiviral activity on the bovine and murine cells tested.

Interferon epsilon may be produced by stimulating primary, diploid epithelial cells of human origin with a virus. Such cells may be cultured, for example, in accordance with the procedure disclosed in U.S. Pat. No. 4,016,036 to Green et al., the disclosure of which is incorporated herein by reference. When the new interferon is produced in this way, other known interferons are co-produced. This fact, coupled with the fact that IFN epsilon has no detectable antiviral activity on the cell type normally used in interferon assays, i.e., fibroblasts, explains why the existence and identity of this new substance theretofore has eluded those skilled in the art.

The new interferon may also be produced in naturally or artificially transformed eukaryotic cells containing the gene coding for epsilon interferon that is active in normal epithelial cells. It may also be produced in cells modified by recombinant DNA techniques, i.e., cells containing a transcriptionally competent foreign DNA including the gene coding for interferon epsilon that is active in human epithelial cells.

Interferon epsilon can be distinguished readily from other interferons by employing a keratinoctye assay technique described in a co-pending patent application Ser. No. 628,612, filed 7-12-81, entitled "Assay for Interferon Epsilon", filed herewith. The teachings of this commonly-assigned patent application are hereby incorporated by reference. The keratinocyte assay is based on the observation that of all known interferons, only interferon epsilon is active when used to treat epithelial cells yet has no detectably activity when used to treat other types of cells.

Accordingly, it is an object of the invention to provide a new type of antiviral substance useful, for example, in protecting human epithelial cells from virus attack. Another object is to provide a method of producing a new interferon of the type indigenous to normal, healthy, human epithelial tissue. Yet another object is to provide a method of treatment of viral infection or tumor growth in epithelial tissue. Another object is to provide a type of interferon which is specific for human epithelial cells. These and other objects and features of the invention will be apparent from the following description and from the appended claims.

DESCRIPTION

Figure 1:
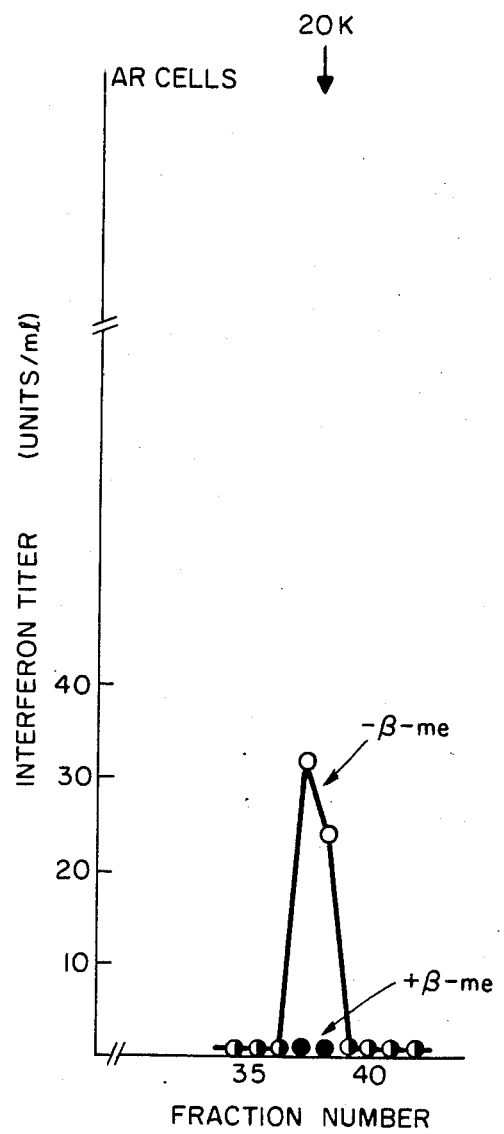
FIG. 1 is a graph showing electrophoresis of the epithelial interferon of the invention.

Broadly, to produce interferon epsilon, normal human epithelial cells may be cultured in vitro, for example, in accordance with the method of Green et al. The cells are then subjected to an IFN induction technique by exposure to certain viruses. After a short incubation, typically on the order of and hour, the inducer may be removed, and the cells placed in normal, fresh growth or maintenance medium and incubated, e.g., for 24 hours. Exposure of the cells to the inducer triggers expression of the cell's gene(s) coding for epsilon interferon production. During the subsequent incubation, the cell will synthesize and secrete interferon epsilon. At this point the medium is harvested and if assayed by, for example, the method described in the above-referenced co-pending application entitled "Assay for Interferon Epsilon" will be found to contain interferon epsilon antiviral activity.

Epithelial cells stimulated in this way produce other interferons which also have antiviral activity in epithelial cells. Accordingly, these contaminating materials must be removed in order to examine the properties of epsilon interferon. This may be done by neutralizing the activity of the contaminating interferon with antibodies, i.e., by mixing anti alpha, anti beta, and/or anti gamma antibodies with the harvested medium. Of course, other purification steps can produce a more concentrated, higher activity preparation.

The product which results from this procedure shows no cross-reactivity with antibody to alpha interferon, beta interferon, or gamma interferon in neutralization experiments. It is stable at pH 2, and its activity is destroyed by proteolytic enzymes. It is believed to be a glycosylated protein. It has an apparent molecular weight of about 20,000 daltons (as determined by SDS polyacrylamide gel electrophoresis) when glycosylated. The new interferon exhibits marked activity in human epithelial cells but no detectable activity in fibroblast or other types of cells. These characteristics mark interferon epsilon as a unique substance.

Interferon epsilon can be produced from normal epithelial cells derived, for example, from human epidermis, conjunctiva, vagina, and esophagus, employing "normal induction" (Field et al., *Proceedings of the National Academy of Sciences*, Vol. 58, p. 1004–1009, 1967) with Newcastle Disease Virus, (Baron and Issacs, *British Medical J.*, Vol. 56, pp. 18–20, 1962) and with Sendai virus (parainfluenza-1, Gresser, *Proceedings of the Society of Experimental and Biological Medicine*, Vol. 108, pp. 303–307, 1961). Production levels vary with the type of inducer employed and with the various modifications of the induction techniques. It appears that younger keratinocyte cells produce more interferon epsilon then aged cells. Newcastle Disease Virus works well. Other viruses which may be useful are set forth in the following table.

TABLE I

| Virus | References |
|---|---|
| Influenza-A | Gresser and Dull (1964); Andrews (1961) |
| Parainfluenza-3 | Chany (1960) |
| Measles | Petralli, Merigan, and Wilbur (1965a); DeMaeyer and Enders (1961) |
| Mumps | Cantell (1961); |
| Waddell, Wilbur, | |
|  | and Merigan (1968) |
| Rubella | Neva and Weller (1964) |
| Respiratory syncytial | Ray, Gravelle, and Chin (1967); Moehring and Forsyth (1971) |
| Rabies virus | Wiktor et al. (1972) |
| Vesicular stomatitis | Marcus and Sekellick (1977); Vilcek, Yamazaki and Havell (1977) |
| Chikungunya | Zimmermann et al. (1972) |
| Sindbis | Gresser and Enders (1962) |
| Western equine encephalitis | Luby, Sanders, and Sulkin (1971) |
| Yellow fever | Wheelock and Sibley (1965); Wheelock and Edelman (1969) |
| Poliovirus-Type 1 | Gresser, Chany, and Enders (1965) |
| Poliovirus-Type-2 | Smorodintsev et al. (1970); Ho and Enders (1959a,b) |
| Encephalomyocarditis | Stewart II, Gosser, and Lockart (1971-a) |
| Rhinovirus-2 | Smorodintsev et al. (1971a); Fiala (1972) |
| Rhinovirus-12 | Gatmaitan, Stanley, and Jackson (1973) |
| Reovirus-2 | Oie, Loh, and Ratnayake (1973) |
| Blue tongue | Jameson and Grossberg (1977) |
| Adenoviruses | Lysov et al. (1971) |
| Varicella-zoster | Vaczi, Horvath, and Hadhazy (1965) |
| Human cytomegalovirus | Vaczi, Horvath, and Hadhazy (1965); Glasgow (1974) |
| Herpes simplex | Rasmussen et al. (1974) |
| Vaccinia | Wheelock (1964); Epstein, Stevens, and Merigan (1972) |

Interferon epsilon is active as an antiviral substance when used to treat epithelial cells, but has no detectable activity when used to treat other human cell types. In contrast, beta interferon (of human fibroblast cell origin) is most effective in treating human fibroblast cells or tissue, and has lower antiviral properties with respect to human epithelial cells. Accordingly, the following procedure may be employed to protect human epithelial cell types or tissues from viral infection, and to arrest multiplication of a virus which has infected a given cell type or tissue.

First, a culture of epithelial cells, e.g., keratinocytes, is grown by conventional techniques such as the Green technique referred to above. The cells of the culture are then treated to induce expression of the gene coding responsible for the production of interferon epsilon. This may be done, for example, by conventional IFN induction techniques. The product is then harvested, typically from the medium after incubation and purified. The product may be used as an effective antiviral substance for treatment of the cell or tissue type in question.

One unit of interferon epsilon may be defined as the concentration which protects one half the cells in a human keratinocyte cell culture from challenge by a virus introduced to the culture at a concentration of one pfu/cell. The number of units of interferon present in a given preparation may be assayed by first removing any contaminating interferon activity by neutralization with antibodies, serially diluting the preparation, incubating cultures of keratinocytes with the respective diluted samples, and then challenging the samples with a virus. The number of units present in the undiluted sample is determined by assessing which culture contains 50 percent living cells and then multiplying by the dilution factor of the preparation which was incubated with the culture.

Significant quantities of this new antiviral substance can also be produced by two additional known cellular techniques. The first involves the use of chemically, virally, or spontaneously transformed eukaryotic cells such as epithelial cells. The second employs currently established recombinant DNA techniques similar to those currently employed in the production of alpha and beta interferons.

In the first method, transformed cells capable of producing interferon epsilon can be obtained by employing one of two techniques: in vivo or in vitro. The first technique (in vivo) involves the direct isolation from fresh tissue of transformed epithelial cell types; the second technique (in vitro) involves a selection procedure in which a strain of normal human diploid epithelial cells is either cultured on a long term basis until a small but detectable number of cells in the population undergoes spontaneous transformation, or the initial strain is treated for a brief period of time with a virus or a known mutagen such as EMS, MMS, or MNNG to increase the frequency of transformation. Certain of the cells transformed by either of the two in vitro methods described will contain a transcriptionally competent gene coding responsible for the production of interferon epsilon.

Transformed cultures thus obtained may be induced to produce interferon epsilon by employing standard induction techniques as described previously for normal human diploid epithelial cells.

In the second technique, the mRNA synthesized in epithelial cells in response to the IFN induction is extracted from the cells, optionally purified by ultracentrifugation or the like to obtain an mRNA fraction of increased specificity, and the extract is used as a template for the synthesis of complementary DNA (cDNA). The cDNA may be produced using the Avian Myoblastosis reverse transcriptase enzyme. The final resulting product of this process, double stranded complementary DNA (dscDNA), which includes the sequence coding for the synthesis of interferon epsilon, and a bacterial or eukaryotic vector are then treated with a restriction enzyme which cleaves the DNA and produces bonding sites by which the dscDNA and the vector may be attached. The vector and DNA are then mixed together, annealed, and covalently bonded employing a ligase enzyme. At this point the recombinant vector preparation is used to transform either a bacterial or eukaryotic cell. The transformed cells thus contain the DNA complementary to all or part of the RNA originally contained in the epithelial cells during their interferon epsilon production stage.

These recombinant vectors are then incubated with an appropriate cell type which permits the vector to operate. This results in a cell population which includes one or more individual cells capable of synthesizing and secreting interferon epsilon. The cell population is then screened for a subpopulation of cells having an exogenous, transcriptionally competent gene which produces interferon epsilon, and this subpopulation is cultured to establish a cell line capable of producing relatively large quantities of interferon epsilon.

Further particulars of this recombinant DNA technique may be found, for example, in the following references, the disclosures of which are incorporated herein by reference.

1. U.S. Pat. No. 4,237,224 to Cohen et al entitled "Process For Producing Biologically Functional Molecular Chimeras".

2. Scheller, R. et al, 1977, *Clones of Individual Repetitive Sequences from Sea Urchins DNA Constructed with Synthetic Eco $R_1$ Sites, Science*, Vol. 196, pp. 197-200;

3. Blattner, F. et al, 1977, *Charon Phages: Safer Derivatives of Bacteriophage Lambda for DNA Cloning, Science*, Vol. 196, pp. 161-169;

4. Broach, J. R., and Hicks, J. B., 1980, *Replication and Recombination Functions Associated with Yeast Plasmid, 2 Micron Circle, Cell*, Vol. 21, pp. 501-508; and 5. Hamer, D. 1981, *Synthesis Processing and Secretion of Eukaryotic Proteins in the SV40—Monkey Cell System*, Recombinant DNA Abstracts, Vol. 1, p. 4.

The invention will be further understood from the following, non-limiting examples.

EXAMPLE 1

An epithelial cell culture of epidermal origin (keratinocytes) obtained from the laboratory of Dr. Howard Green at Massachusetts Institute of Technology was grown to a density of $1-2 \times 10^5$ cells per cm$^2$ and used to produce interferon epsilon employing the Newcastle Disease Virus (NDV) induction method (Baron and Issacs, supra). The virus used was the Bankowski strain of NDV available from Poultry Health Laboratories, Davis, Calif. Four 1 ml samples of a minimum essential medium (MEM,Gibco) containing 2 percent heat inactivated fetal calf serum ("HIFCS") and NDV to multiplicities of infection ranging from 0 to 250 virus pfu/cell in the test samples were prepared and incubated. The cell cultures were incubated for 24 hours. The medium was then harvested, acidified to pH 2 with 0.1N HCl, and stored at 4° C. for 5-6 days to inactivate the NDV.

EXAMPLE 2

The crude interferon prepared in accordance with Example 1 was tested for antiviral activity after neutralization of interferon alpha, interferon beta and interferon gamma with antibodies specific for each of the three known interferon types. Neutralization titrations of each interferon were carried out using anti-IFN alpha (NIH), anti-IFN beta (NIH and Y. H. Tan, Calgary University, Calgary, Alberta, Canada), anti-IFN gamma (S. Baron), and mixtures of these antisera. The remaining neutralized preparations were then tested on fibroblast (Human FS-4) and epithelial (Human AR) cultures. The results indicated that interferon epsilon had no detectable antiviral activity on fibroblasts but showed activity against viruses in epithelial cells.

The table below summarizes a complete battery of neutralization and antiviral activity tests:

TABLE I

ANTIVIRAL ACTIVITY OF INTERFERON PREPARATIONS ON HUMAN FS-4 AND AR CELLS

| Sample | Treatment[1] | | | Interferon titer[2] (units/ml) | |
|---|---|---|---|---|---|
| | Anti-α | Anti-β | Anti-γ | Human FS-4 | Human AR |
| IFN-ε | − | − | − | 128 | 64 |
| IFN-ε | + | − | − | 48 | 32 |
| IFN-ε | − | + | − | 24 | 32 |
| IFN-ε | − | − | + | 192 | 32 |
| IFN-ε | + | + | − | <4 | 32 |
| IFN-ε | + | + | + | <4 | 32 |
| IFN-α | − | − | − | 64 | 4 |
| IFN-β | − | − | − | 128 | 16 |
| IFN-α/β | − | − | − | 512 | 16 |
| IFN-γ | − | − | − | 32 | 16 |
| IFN-α/β/γ | − | − | − | 384 | 64 |
| IFN-α/β/γ | + | − | − | 128 | 48 |
| IFN-α/β/γ | − | + | − | 256 | 16 |
| IFN-α/β/γ | − | − | + | N.D. | 16 |
| IFN-α/β/γ | + | + | − | <4 | <4 |
| IFN-α/β/γ | + | + | + | <4 | <4 |

[1]The samples were incubated with excess antiserum, as indicated, at 37° C. for 1 hr. before being assayed for interferon activity.
[2]The interferon titer was determined by a viral cytopathic assay.
[3]N.D. — no data It is apparent from the data that interferon alpha and interferon beta were co-produced with interferon epsilon. Note that neutralization with alpha antibody alone or beta antibody alone reduced the units of interferon activity in both the fibroblast and keratinocyte cultures. Neutralization with both and with a mixture of alpha, beta, and gamma antibodies destroyed all antiviral activity of the epsilon preparation on fibroblasts while 32 units/ml activity remained in the keratinocyte cells. This demonstrates the presence of interferon epsilon and confirms that it has selective activity on epithelial cell cultures.

EXAMPLE 3

This example shows the stability of interferon epsilon to acid pH. Interferon epsilon was produced by induction of human epidermal cells with NDV in accordance with example 1. When the medium was harvested, it was divided into three portions. The virus was inactivated in the first portion as described in example 1 by acidifying to pH 2 with HCl. The second portion was filtered for 5 days through a Millipore 01310 filter (100,000 molecular weight limit, Millipore Corp., Bedford, MA) to remove the virus. The third portion was filtered through a Millipore PTMK01310 filter, 100,000 molecular weight limit, which had been previously soaked for 4 hours in a 1 percent solution of BSA. In each case the resulting medium was assayed for both interferon epsilon and for the presence of residual virus. None of the samples showed any viral activity and each sample contained the same amount of interferon epsilon activity.

EXAMPLE 4

The effect of culture age of keratinocytes and multiplicity of infection of the inducing virus on the production of epsilon interferon was studied. The results are summarized below in Table II:

TABLE II

THE EFFECT OF CULTURE AGE
AND M.O.I. ON IFN-E PRODUCTION

| M.O.I.[1] | Interferon titer[2] (units/$10^6$ cells) | | |
|---|---|---|---|
| | 14 days | 21 days | 27 days |
| 0 | <6 | <3 | <4 |
| 0.1 | 10 | <3 | <4 |
| 1 | 53 | 2 | 8 |
| 2 | 79 | 6 | 16 |
| 5 | 210 | 6 | 16 |
| 10 | 157 | 6 | 16 |
| 20 | 210 | 18 | 32 |
| 50 | 210 | 9 | 32 |
| 70 | ND[3] | 12 | 32 |
| 90 | ND | 9 | 32 |
| 100 | 79 | ND | ND |
| 250 | 79 | ND | ND |

[1]Multiplicity of infection
[2]Interferon samples were incubated with excess interferon alpha and beta anti sera before assayed for activity on keratinocytes.
[3]N.D. — No data Table II shows that, at least for keratinocyte-type epithelial cells, younger cells, i.e., almost confluent 14-day old cells, produce more interferon epsilon than do older cells. This result is in contrast to the experiments with other forms of interferon, where it is typically found that older cells produce higher titers. This phenomenom may be explained, in part, by the characteristic accumulation of keratin in keratinocyte cells as they age. The table also shows that IFN epsilon production is highest when using virus concentrations (multiplicity of infections) in the range of 5 to 20.

EXAMPLE 5

Unfractionated interferon epsilon was first centrifuged at 300 xg for 20 minutes. The supernatant was mixed end over end on a Fisher Rotarack with controlled pore glass (C.P.G) (Electronucleonics, Inc.) at 4° C. 0.28 gms of controlled pore glass was used per 30 ml. of culture supernatant. After 3 hrs., the supernatant was removed and the controlled pores glass beads were packed in a column (2.5×3.1 cm.). The column was first washed with 4 column volumes of PBS followed by 4 column volumes of 1.0M NaCl-20 mM phosphate buffer, ph 7.4. The interferon epsilon was eluted with 4 columns volumes of 50 percent v/v ethylene glycol -1.0M NaCl-20 mM phosphate buffer ph 7.4 and collected into an equal volume of 1.0M NaCl-20 mM phosphate buffer to give a final concentration of ethylene glycol of 25 percent. The interferon epsilon containing fraction was concentrated by ultrafiltration to 1.0 to 1.6 mls and applied to a polyacrylamide-agarose (Ultragel AcA54) column (1.6×85 cm.) equilibrated with 25 percent ethylene glycol (V/V) -1.0M NaCl-20 mM phosphate buffer 7.4. The interferon epsilon was then eluted with equilibrating buffer at a flow rate of 6.0 mls per hour.

Interferon epsilon may be purified and concentrated by affinity chromatography on a number of immobilized ligands. These include, but are not limited to, reactive red agarose, phenyl sepharose (Sigma Chemical Co., St. Louis, Mo.), procion red agarose, phenyl agarose (BRL, Gaithersburg, Md.), Glycogel B, N-(3-carboxypropionyl) aminodecane (CPAD) agarose and N-pyromellitylaminodecane (PMAD) agarose (Pierce Chemical Co., Rockford, Ill.). Interferon epsilon also can be purified on a column containing immobilized anti-interferon epsilon.

EXAMPLE 6

Epithelial interferon materials produced in accordance with Example 1 and partially purified in accordance with Example 5, were subjected to molecular weight analysis using SDS gel electrophoresis according to the method of Lamelli. The samples were incubated at room temperature for 1 hour in the presence of 1.0 percent SDS, 0.05M tris-HCl (pH 6.8) buffer, 10 percent (v/v) glycerol, and 0.001 percent bromo phenol blue, loaded onto 12.5 percent polyacrylamide gels, and run for approximately 16 hours. After electrophoresis the lanes containing the molecular weight standards were stained. interferon containing lanes were sliced into 3 mm slices, and extracted by shaking with 0.5 ml PBS containing 0.5 percent SDS for 20 hours at room temperature. Assays of these fractions were performed and the molecular weight of the principal activity peak associated with interferon epsilon was calculated to be approximately 20,000 by comparison of its position on the gel with the molecular weight standards.

In FIG. 1, interferon epsilon activity is shown clearly in AR epithelial (keratinocyte) cells. The protein corresponding to the epithelial activity has an apparent molecular weight of about 20,000 and is also dramatically reduced in activity by treatment with beta-mercaptoethanol.

Having demonstrated the existence of a new type of interferon and described its production, purification and characterization, it should be clear that those skilled in the art may make various changes, modifications or additions to the methods and materials taught herein without departing from the spirit or scope of the following claims.

We claim:

1. An interferon preparation having antiviral activity, said preparation being characterized in that:
   (i) it is made by a living cell containing a gene active in human epithelial cells;
   (ii) its antiviral activity is specific to human epithelial cells;
   (iii) it is antigenically distinct from interferon alpha, interferon beta, and interferon gamma;
   (iv) its antiviral activity is stable at pH 2 and is destroyed by proteolytic enzymes; and
   (v) it has no detectable antiviral activity in human fibroblast cells.

2. The interferon preparation of claim 1 wherein said living cell is a human keratinocyte cell.

3. The interferon preparation of claim 1 further characterized as having a molecular weight of about 20,000 by SDS polyacrylamide gel electrophoresis.

4. The interferon preparation of claim 1 further characterized in that it has antiviral activity in human keratinocytes.

5. The interferon preparation of claim 1 further characterized in that it has no antiviral activity in murine or bovine cells.

6. A process for producing an interferon comprising the steps of:
   A. producing a culture of living cells containing a gene active in human epithelial cells;
   B. incubating said cells in a medium under conditions to promote synthesis of interferon;
   C. harvesting said medium; and
   D. purifying an interferon from said medium, said interferon being characterized in that
   (i) its antiviral activity is specific to human epithelial cells;
   (ii) it is antigenically distinct from interferon alpha, interferon beta, and interferon gamma;
   (iii) its antiviral activity is stable at pH 2 and is destroyed by proteolytic enzymes, and
   (iv) it has no detectable antiviral activity in human fibroblast cells.

7. The process of claim 6 wherein said culture of living cells is a human epithelial cell culture and, prior to step B, a virus is used to induce said cells to produce said interferon.

8. The process of claim 7 wherein the virus is Newcastle Disease virus.

9. The process of claim 7 wherein said cell culture is grown from cells sampled from a human epithelial tissue.

10. The process of claim 7 wherein said cell culture is grown from human keratinocytes.

11. The process of claim 6 wherein a contaminant selected from the group consisting of interferon alpha, interferon beta, interferon gamma, and mixtures thereof is present in said harvested medium, and said purifying step includes the step of removing the activity of said contaminant interferon.

12. A method of treating human epithelial cells to inhibit virus infection, said method comprising the step of:
   contacting the cells to be treated with an effective amount of the interferon preparation of claims 1, 2, 3, 4 or 5 to inhibit said virus infection.

13. The method of claim 12 comprising contacting human keratinocyte cells with said interferon preparation.

* * * * *